United States Patent
Boykin et al.

(10) Patent No.: US 7,071,338 B2
(45) Date of Patent: Jul. 4, 2006

(54) PROCESS FOR THE SYNTHESIS OF BIS-ARYL DIAMIDOXIME COMPOUNDS

(75) Inventors: David W. Boykin, Altanta, GA (US); Mariappan Anbazhagan, Atlanta, GA (US); Richard R. Tidwell, Pittsboro, NC (US)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 10/722,085

(22) Filed: Nov. 25, 2003

(65) Prior Publication Data

US 2004/0127721 A1    Jul. 1, 2004

Related U.S. Application Data

(60) Provisional application No. 60/429,823, filed on Nov. 27, 2002.

(51) Int. Cl.
*C07D 207/335* (2006.01)
*C07D 307/52* (2006.01)
*C07D 333/22* (2006.01)

(52) U.S. Cl. .................. 548/561; 549/74; 549/491
(58) Field of Classification Search ............... 548/561; 549/74, 491
See application file for complete search history.

(56) References Cited

U.S. PATENT DOCUMENTS

| | | | |
|---|---|---|---|
| 5,594,138 A | 1/1997 | Dykstra et al. | 540/596 |
| 5,602,172 A | 2/1997 | Boykin et al. | 514/461 |
| 5,843,980 A | 12/1998 | Hall et al. | 514/438 |
| 6,025,398 A | 2/2000 | Hall et al. | 514/633 |
| 6,326,395 B1 | 12/2001 | Tidwell et al. | 514/461 |
| 6,423,737 B1 | 7/2002 | Hall et al. | 514/399 |
| 6,635,668 B1 | 10/2003 | Tidwell et al. | 514/394 |

OTHER PUBLICATIONS

International Preliminary Examination Report corresponding PCT Appl. No. PCT/US03/37788 dated on Jul. 8, 2004.
Ansede et al., "*O*- Alkoxuamidine Prodrugs of Furamidine: In Vitro Transport and Microsomal Metabolism as Indicators of in Vivo Efficacy in a Mouse Model of *Trypanosoma brucei rhodesiense* Infection", *Journal of Medical Chemistry*, 47:4335-4338, 2004.
Boykin et al., "Anti-Pneumocystis Activity of Bis-Amidoximes and Bis-O-Alkylamidoximes Prodrugs", *Bioorganic & Medical Chemistry Letters*, vol. 6, No. 24, pp. 3017-3020, (1996).
Zhou et al., "Enhanced Permeability of the Antimicrobial Agent 2,5-Bis (4-Amidinophenyl) Furan across Caco-2 Cell Monolayers via Its Methylamidoxime Prodrug", *Pharmaceutical Research*, vol. 19, No. 11, pp. 1689-1695, (Nov. 2002).
Anbazhagan et al., "Palladium-Catalyzed N-arylation of O-methylamidoximes", *Elsevier Science Ltd.*, pp. 4221-4224, (2002).
Das et al., "Synthesis and Antiprotozal Activity of 2,5-Bix (4-guanylphenyl)furans", *Journal of Medicinal Chemistry*, vol. 20, No. 4, pp. 531-536, (1977).
Tidwell et al., "Dicationic DNA Minor Grove Binders as Antimicrobial Agents", in *Small Molecules DNA and RNA Binders: From Synthesis to Nucleic Acid Complexes* (Demeunynck et al.,eds.) Wiley-VCH: 416-460, New York, Dec., 2002.

*Primary Examiner*—Taofiq Solola
(74) *Attorney, Agent, or Firm*—Jenkins, Wilson, Taylor & Hunt, P.A.

(57) ABSTRACT

Bis-aryl diamidoxime compounds, such as 2,5-bis [4-hydroxy and 4-O-alkylamidinophenyl] furans, can be prepared from 2,5-bis tri-alkylstannanes via a one step palladium-catalyzed cross reaction. Bis-aryl diamidoxime compounds, such as 2,5-bis [4-hydroxy and 4-O-alkylamidinophenyl] furans, are useful as therapeutic compounds. The disclosed process is scalable, simpler, more economic and more feasible than other presently known methods of preparing 2,5-bis [4-hydroxy and 4-O-alkylamidinophenyl]furans and other bis-aryl diamidoxime compounds.

9 Claims, No Drawings

PROCESS FOR THE SYNTHESIS OF BIS-ARYL DIAMIDOXIME COMPOUNDS

RELATED APPLICATIONS

This application claims the benefit of U.S. Provisional Patent Application Ser. No. 60/429,823, filed Nov. 27, 2002; the disclosure of which is incorporated herein by reference in its entirety.

TECHNICAL FIELD

The present invention relates to the preparation of bis-aryl diamidoxime compounds in general, and more particularly to methods of preparing bis-aryl diamidoxime compounds by employing cross coupling reactions.

| Abbreviations | |
|---|---|
| Ac | acetyl |
| Bu | butyl |
| DMSO | dimethyl sulfoxide |
| Et | ethyl |
| KOBut | potassium butoxide |
| Me | methyl |
| PCP | Pneumocystis carinii pneumonia |
| Ph | phenyl |
| Pr | propyl |
| rt | room temperature |
| TLC | thin layer chromatography |

BACKGROUND ART 2,5-Bis [4-O-methoxyamidinophenyl] furan, which has the structure Compound 1

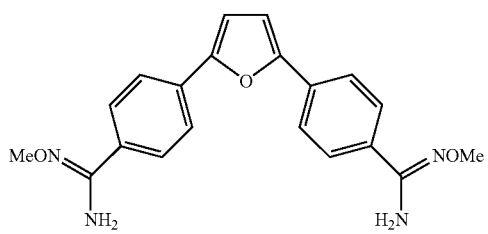

is a prodrug of furamidine, and is effective when administered orally in an immunosupressed rat model for *Pneumocystis carinii pneumonia* (PCP). It is also effective against mouse models of human African trypanosomiasis (Boykin et al., (1996) *Bioorg. Med. Chem. Lett.* 6:3017; Tidwell & Boykin, in *Small Molecule DNA and RNA Binders: From Synthesis to Nucleic Acid Complexes* (Demeunynck et al., eds.) Wiley-VCH, New York, 2002). Compound 1 is currently in Phase II clinical trials against both of these diseases (Tidwell & Boykin, in *Small Molecule DNA and RNA Binders: From Synthesis to Nucleic Acid Complexes* (Demeunynck et al., eds.) Wiley-VCH, New York, 2002). It has been shown that 2,5-bis [4-O-methoxyamidinophenyl] furan (Compound 1) and 2,5-bis [4-hydroxyamidinophenyl] furan, which has the chemical structure Compound 4

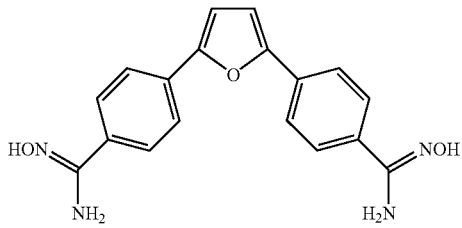

were approximately equally effective against PCP when administered orally. However, the closely related analog 2,5-bis [4-O-ethoxyamidinophenyl] furan, which has the structure Compound 2

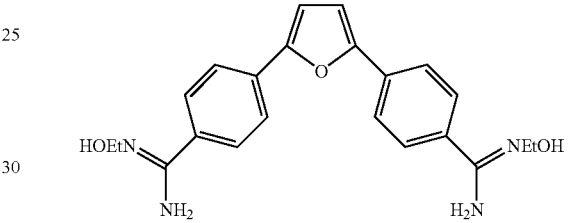

was not effective (Boykin et al., (1996) *Bioorg. Med. Chem. Lett.* 6:3017).

The prior synthesis of Compound 1 and analogs involved the reaction of 2,5-bis [4-cyanophenyl] furan under Pinner-type conditions to form the corresponding imidate ester, which was then allowed to react with the appropriate hydroxylamine (Boykin et al., (1996) *Bioorg. Med. Chem. Lett.* 6:3017). The Pinner process (Pinner, (1883) *Chem. Ber.* 16:1643–1655; see also Walz et al., (1977) *Macromol. Chem.* 178:2527–2534) is cumbersome, since rigorous exclusion of water is essential. When the Pinner process is employed to prepare Compound 1 and related compounds, the process is further complicated due to the very low solubility of 2,5-bis [4-cyanophenyl] furan, necessitating long reaction times, on the order of 3–7 days.

Thus, what is needed is a method of synthesizing bis-heteroaryl compounds, such as 2,5-bis [4-hydroxy and 4-O-alkylamidinophenyl] furans having the general structure

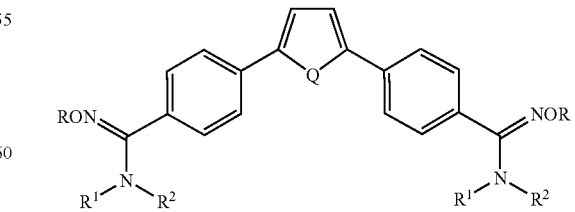

that is simple and economical, and that avoids the drawbacks of the Pinner process. The methods of the present invention address these and other needs in the art.

SUMMARY OF THE INVENTION

A method of preparing a bis-aryl diamidoxime compound is disclosed. In one example, the method comprises: (a) contacting an amidoxime aryl halide with a 2,5-bis tri-alkylstannane under an anhydrous gas to form a first reaction mixture; (b) adding an anhydrous aprotic solvent and a palladium catalyst to the first reaction mixture to form a second reaction mixture; and (c) refluxing the second reaction mixture for a period of time, whereby a bis-aryl diamidoxime compound is prepared.

In one embodiment, the bis-aryl diamidoxime compound comprises the structure:

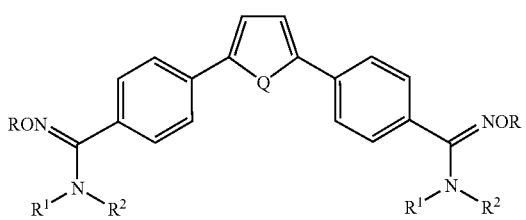

wherein R, $R^1$, and $R^2$ are the same or different and are selected from the group consisting of H, aryl, linear alkyl, cyclic alkyl, and branched alkyl; Q is selected from the group consisting of O, S, NH and $CH_2$; and pharmaceutically acceptable salts thereof. In another embodiment, the amidoxime aryl halide is selected from the group consisting of ρ-bromobenzamidoxime, O-methyl-ρ-bromobenzamidoxime and O-n-propyl-ρ-bromobenzamidoxime, and the 2,5-bis tri-alkylstannane comprises a moiety selected from the group consisting of furan, thiophene, pyrrole, and cyclopentadiene. In other embodiments, the anhydrous gas is selected from the group consisting of nitrogen and argon and the anhydrous aprotic solvent is selected from the group consisting of dioxane and dimethylformamide. In yet another embodiment, the palladium catalyst is tetrakis(triphenylphosphene)palladium(0), and in a further embodiment the refluxing is for a period of about 16 hours.

In still another embodiment of the present invention, the method optionally further comprises: (a) following the refluxing, removing the aprotic solvent to form a residue; (b) diluting the residue into a nonpolar solvent to form a solvated residue; (c) filtering the solvated residue to form a filtered residue; (d) washing the filtered residue with a wash solvent to form a washed residue; and (e) drying the residue. The nonpolar solvent is selected from the group consisting of ethers, alkanes and methylene chloride, for example, and the wash solvent can be selected from the group consisting of an ether, an alkane, methylene chloride, ethyl acetate, ethanol and combinations thereof.

Some of the objects of the invention having been stated hereinabove, other objects will be evident as the description proceeds, when taken in connection with the accompanying drawings as best described hereinbelow.

DETAILED DESCRIPTION OF THE INVENTION

Throughout the specification and claims, a given chemical formula or name shall encompass all stereoisomers.

As used herein the term "alkyl" means $C_{1-20}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Lower alkyl" refers to an alkyl group having 1 to about 8 carbon atoms, i.e. 1, 2, 3, 4, 5, 6, 7 or 8 carbon atoms. "Higher alkyl" refers to an alkyl group having about 10 to about 20 carbon atoms.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulphur or substituted or unsubstituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to a linear alkyl chain.

As used herein, the term "aryl" means a cyclic aromatic comprising about 5 to about 10 carbon atoms, including 5 and 6-membered hydrocarbon and heterocyclic aromatic rings. The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The compounds disclosed herein can be administered in the form of pharmaceutically acceptable salts. The term "pharmaceutically acceptable salt" is intended to include all acceptable salts. Examples of some acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of a compound disclosed herein, pharmaceutically acceptable salts of the compounds include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts can be prepared by standard procedures, e.g. by reacting a free acid with a suitable organic or inorganic base, or alternatively by reacting a free base with a suitable organic or inorganic acid.

As used herein, the term "reflux" and grammatical derivations thereof means boiling a liquid in a container with which a condenser is associated, thereby facilitating continuous boiling without loss of liquid, due to the condensation of vapors on the interior walls of the condenser.

In one aspect of the present invention, the application of Stille cross-coupling chemistry for the preparation of bis-aryl diamidoxime compounds, such as 2,5-bis [4-hydroxy and 4-O-alkylamidinophenyl] furans, is disclosed. Generally, the methods of the present invention comprise charging a dried round-bottomed flask with an amount of a 2,5-bis tri-alkylstannane and an amount of an amidoxime under a gas, such as nitrogen. A volume of solvent, such as dioxane (e.g., anhydrous dioxane) is then added to the flask as well as an amount of catalyst. The mixture is heated at reflux for a desired period of time. After a desired level of consumption of the amidoxime has been reached, the reaction mixture is cooled and the solvent removed. The residue can then be optionally diluted and filtered, for example through a layer of CELITE® (available from World Minerals Corp. of Santa Barbara, Calif., USA). The layers are then combined and optionally washed and the solvent removed under reduced pressure. The crude product can then be purified.

Thus, in one aspect of the present invention, a method of preparing bis-aryl diamidoxime compounds having the structure

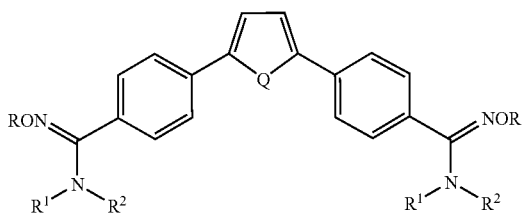

wherein R, $R^1$, and $R^2$ are the same or different and are selected from the group consisting of H, aryl, linear alkyl, cyclic alkyl, and branched alkyl; Q is selected from the group consisting of O, S, NH and $CH_2$; and pharmaceutically acceptable salts thereof, is disclosed. In one embodiment of the method, an amidoxime aryl halide is contacted with a 2,5-bis tri-alkylstannane under a gas to form a first reaction mixture. As detailed further in the Laboratory Examples, a list of representative, but non-limiting, list of amidoxime aryl halides includes p-bromobenzamidoxime, O-methyl-p-bromobenzamidoxime and O-n-propyl-p-bromobenzamidoxime. Any inert gas, such as nitrogen or argon for example, can be employed. Representative 2,5bis-tri-alkylstannanes include, but are not limited to, furans, pyrroles, thiophenes, and cyclopentadienes.

An aprotic solvent and a palladium catalyst are then added to the first reaction mixture to form a second reaction mixture. Any aprotic solvent can be employed in the present invention, for example anhydrous dioxane. A representative palladium catalyst is tetrakis(triphenylphosphene)palladium (0). The catalyst can comprise about 5 mol-percent, based on the 2,5bis-tri-alkylstannane, but can also be less, for example about 2 mol-percent.

The second reaction mixture is then heated at reflux for a period of time. The period of time can vary, but in one example, the period of time can be about 16 hours.

Additional steps can be performed, and constitute further embodiments of the present invention. For example, following the refluxing, the aprotic solvent can be removed to form a residue. Any of a variety of approaches can be employed to remove the solvent; rotary evaporators are one such approach. The residue can then be diluted into a nonpolar solvent, such as an ether, an alkane or methylene chloride, for example, to form a solvated residue. The solvated residue can then be filtered to form a filtered residue and washed with a wash solvent to form a washed residue. Suitable wash solvents will be apparent to those of ordinary skill in the art upon a review of the present disclosure. However, representative solvents include an ether, an alkane, methylene chloride, ethyl acetate, ethanol and combinations thereof. The residue can then be dried.

The use of a 2,5-bis-trialkylstannane (e.g., 2,5-bis(tri-n-butylstannyl)furan) in palladium catalyzed cross-coupling reactions provides a convenient one step process for preparation of these molecules, which are difficult to obtain by the Pinner process. For example, the methods of the present invention are simpler and less laborious than the Pinner process. Additionally, the methods of the present invention can provide increased yields over the Pinner process, since in the Pinner process much of the product is lost to water contamination. This can also translate into an economic advantage. Thus, the methods of the present invention provide an attractive, scalable approach to synthesizing these and other amidoximes.

LABORATORY EXAMPLES

The following Laboratory Examples have been included to illustrate preferred modes of the invention. Certain aspects of the following Laboratory Examples are described in terms of techniques and procedures found or contemplated by the present co-inventors to work well in the practice of the invention. These Laboratory Examples are exemplified through the use of standard laboratory practices of the co-inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Example 1

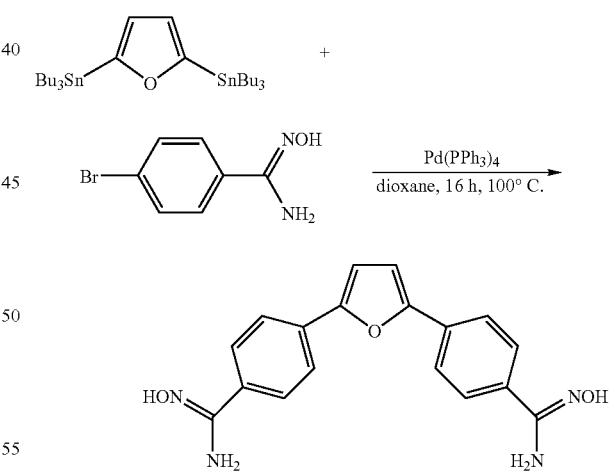

Compound 4

An oven-dried 25 mL round-bottomed flask was charged with 678 mg (1.05 mmol) of 2,5-(bistributylstannyl)furan and 428 mg (2 mmol) of ρ-bromobenzamidoxime under nitrogen. 10 mL of dioxane and 115 mg of tetrakis(triphenylphosphene)palladium(0) was added to the flask and the mixture refluxed for 16 hours. After complete consumption of the amidoxime, as indicated by thin layer chromatography (TLC), the reaction mixture was cooled and the solvent was removed in rotary evaporator. The residue was diluted with ether and filtered. The residue was washed with ether, hexane, methylene chloride, EtOAc, and a volume of ethanol and dried to yield 225 mg (67%) of the product. $^1$H and $^{13}$C NMR analysis of the product provided the following: $^1$H(DMSO-d$_6$): 5.86(br, 4H, 2NH$_2$), 7.13(s, 2H, Furan), 7.76(d, 4H, J=9.0 Hz, Ar), 7.84(d, 4H, J=9.0 Hz, Ar), 9.72(s, 2H, 2NOH); $^{13}$C(DMSO-d$_6$): 108.95, 123.19, 125.87, 130.29, 132.25, 150.43, 152.52. Analysis Calculated for C$_{18}$H$_{16}$N$_4$O$_3$: C 64.28; H 4.76; N 16.66; Found: C 64.10; H 4.81; N 16.53.

Laboratory Example 2

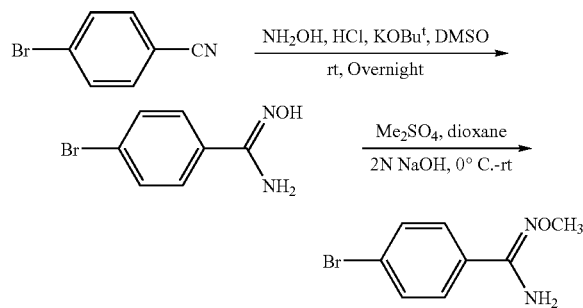

Hydroxylamine hydrochloride was suspended in anhydrous dimethylsulfoxide (DMSO) and the mixture was cooled in an ice bath. Potassium tert-butoxide (KOBut) was added in a portionwise fashion under a nitrogen atmosphere and the solution was stirred at room temperature for one hour. Then, ρ-bromobenzonitrile was added at once and the reaction mixture was stirred overnight at room temperature. It was poured over ice-water, the product was filtered and the ρ-bromobenzamidoxime was recrystallized from ethanol.

The ρ-bromobenzamidoxime was dissolved in dioxane and cooled to 0° C. 2N NaOH solution was added slowly, followed by dimethyl sulfate in dioxane in a dropwise fashion. After the addition, the ice-bath was removed and the mixture stirred at room temperature for one hour. TLC showed the disappearance of the amidoxime, the mixture was extracted with EtOAc (3×mL), combined organic layers were washed with water, brine and dried over Na$_2$SO$_4$. The solution was filtered and the solvent was removed under reduced pressure. The crude product was then purified by passing through a short column.

Laboratory Example 3

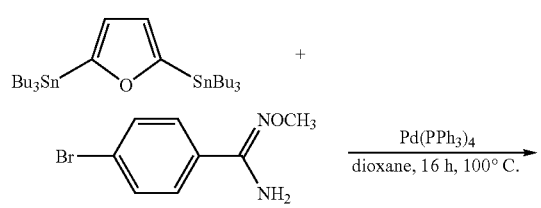

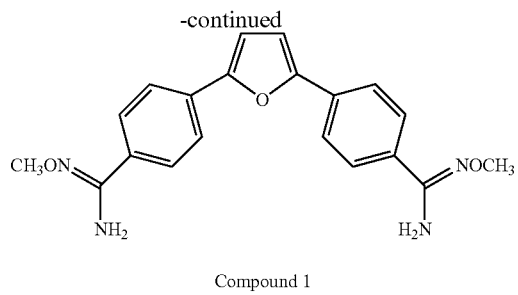

Compound 1

An oven-dried 25 mL round-bottomed flask was charged with 678 mg (1.05 mmol) of 2,5-(bistributylstannyl)furan and 456 mg (2 mmol) of O-methyl-ρ-bromobenzamidoxime under nitrogen. 10 mL of anhydrous dioxane and 115 mg of tetrakis(triphenylphosphene)palladium(0) was added to the flask and the mixture was refluxed for 16 hours. After complete consumption of the amidoxime, as indicated by TLC, the reaction mixture was cooled and the solvent was removed in rotary evaporator. The residue was diluted with EtOAc and filtered through a CELITE® layer (available from World Minerals Corp. of Santa Barbara, Calif., USA). The CELITE® layer was washed with excess of EtOAc. Then the combined EtOAc was washed with water, brine and dried over anhydrous Na$_2$SO$_4$. The solution was filtered and the solvent was removed under reduced pressure. The crude product was purified by flash chromatography using 35–40% ethyl acetate in hexane to yield 212 mg (61%) of the product, Compound 1. $^1$H and $^{13}$C NMR analysis of the product provided the following: $^1$H(CDCL$_3$): 3.75(s, 6H, 2OCH$_3$), 6.10(br, 4H, 2NH$_2$), 7.16(s, 2H, Furan), 7.72(d, 4H, J=6.1 Hz, Ar), 7.81(d, 4H, J=6.1 Hz, Ar); $^{13}$C(CDCl$_3$): 61.51, 108.37, 123.79, 126.18, 131.15, 131.81, 151.41, 153.05. Analysis Calculated for C$_{20}$H$_{20}$N$_4$O$_3$: C 65.93; H 5.49; N 15.78; Found: C 66.13; H 5.52; N 15.32.

Laboratory Example 4

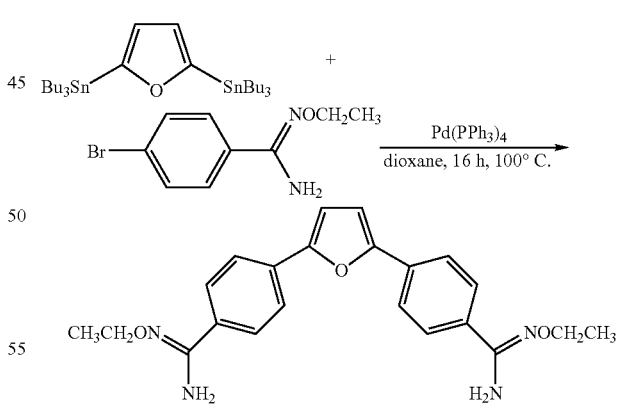

Compound 2

An oven-dried 25 mL round-bottomed flask was charged with 678 mg (1.05 mmol) of 2,5-(bistributylstannyl)furan and 484 mg (2 mmol) of O-n-propyl-ρ-bromobenzamidoxime (see Laboratory Example 2) under nitrogen. 10 mL of anhydrous dioxane and 115 mg of tetrakis(triphenylphosphene)palladium(0) was added to the flask and the mixture was refluxed for 16 hours. After complete consumption of the amidoxime as indicated by TLC, the reaction mixture was cooled and the solvent was removed in rotary evaporator. The residue was diluted with EtOAc and filtered through a CELITE® layer (available from World Minerals Corp. of Santa Barbara, Calif., USA). The CELITE® layer was washed with excess of EtOAc. Then the combined EtOAc was washed with water, brine and dried over anhydrous $Na_2SO_4$. The product was filtered and the solvent was removed under reduced pressure. The crude product was purified by flash chromatography using 35–40% ethyl acetate in hexane to yield 254 mg (65%). $^1H(CDCL_3)$: 1.34(t, 6H, J=6.0 Hz, 2CH3), 4.19(q, 4H, J=6.0 Hz, 2CH$_2$), 4.83(br, 4H, 2NH$_2$), 6.79(s, 2H, Furan), 7.67(d, 4H, J=9.0 Hz, Ar), 7.75(d, 4H, J=9.0 Hz, Ar); $^{13}C(CDCl_3)$: 14.72, 69.13, 108.31, 123.76, 126.15, 131.37, 131.71, 151.25, 153.05. Analysis Calculated for $C_{22}H_{24}N_4O_3 \cdot 2HCl \cdot 2H_2O$: C 52.69; H 6.02; N 11.17; Found: C 52.63; H 5.83; N 11.08.

Results and Discussion of Laboratory Examples 1–4

The palladium-catalyzed reactions of 2,5-bis(tri-n-butyl-stannyl)furan with amidoxime aryl bromides in a dioxane solution at 90–100° C. for 14–18 hours gave 2,5-diaryl-furans in good yields, ranging from 61 to 70% (see Scheme 1 and Table 1). Interestingly, coupling of the 4-bromoben-zamidoxime gave the corresponding bis-amidoxime, which has the structure Compound 4

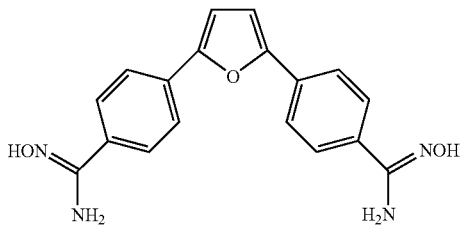

in good yield. In contrast, under N-coupling conditions the benzamidoxime was converted to benzonitrile (Anbazhagan et al., (2002) *Tetrahedron Lett.* 43: 4221) and attempted Heck coupling of 4-bromobenzamidoxime with 2(4-cyanophenyl)furan yielded 2,5-bis(4-cyanophenyl)furan.

Thus, a general method of the present invention can be summarized by Scheme 1. Details of representative embodiments of the methods are presented in Table 1 and more detail regarding these preparations is disclosed herein, particularly in the Laboratory Examples.

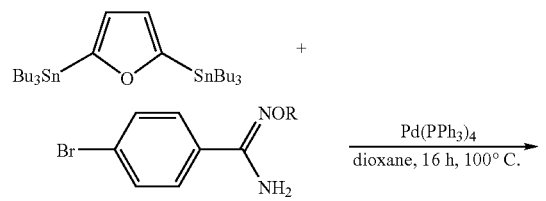

-continued

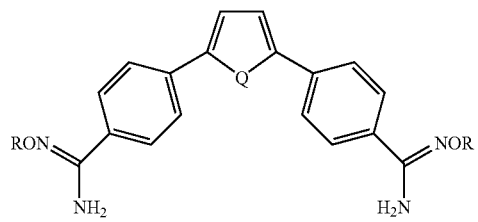

TABLE 1

Amidoxyfurans Synthesized in Laboratory Examples 1–4.

| Compound | R[a] | Q | Temp (° C.) | Reaction Time(h) | % Yield | Mp° C. |
|---|---|---|---|---|---|---|
| 1 | Me | O | 100 | 16 | 61 | 192.5–193 |
| 2 | Et | O | 100 | 14 | 65 | 164–165 |
| 3 | n-Pr | O | 100 | 14 | 70 | 158.5–159.1 |
| 4 | H | O | 100 | 18 | 67 | Over 350 |

[a]Catalyst = about 5 mol-percent Pd(PPh$_3$)$_4$ based on 2,5-bis(tri-n-butylstan-nyl)furan; dioxane used as solvent.

It will be understood that various details of the invention may be changed without departing from the scope of the invention. Furthermore, the foregoing description is for the purpose of illustration only, and not for the purpose of limitation.

What is claimed is:

1. A method of preparing a bis-aryl diamidoxime compound of formula (I):

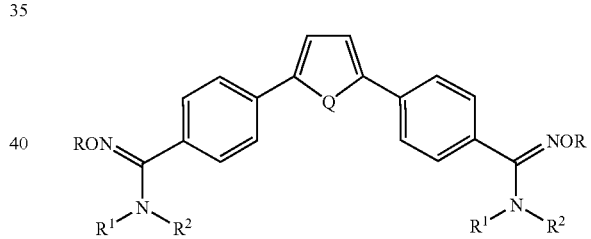

wherein:
R, R$^1$, and R$^2$ are the same or different and are selected from the group consisting of H, aryl, linear alkyl, cyclic alkyl, and branched alkyl;
Q is selected from the group consisting of O, S, NH and CH$_2$; and pharmaceutically acceptable salts thereof;
the method comprising:
(a) contacting an amidoxime aryl halide with a 2,5-bis trialkylstannane compound under an anhydrous gas to form a first reaction mixture, wherein the amidoxime aryl halide has the following structure:

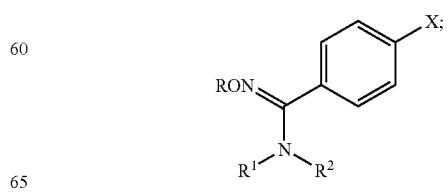

wherein R, R¹, and R² are the same or different and are selected from the group consisting of H, aryl, linear alkyl, cyclic alkyl, and branched alkyl; and X is halogen; and wherein the 2,5-bis trialkylstannane has the following structure:

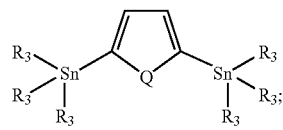

wherein $R_3$ is lower alkyl and Q is selected from the group consisting of O, S, NH and $CH_2$;

(b) adding an anhydrous aprotic solvent and a palladium catalyst to the first reaction mixture to form a second reaction mixture; and (c) refluxing the second reaction mixture for a period of time, whereby a bis-aryl diamidoxime compound of formula (I) is prepared.

2. The method of claim 1, wherein the amidoxime aryl halide is selected from the group consisting of ρ-bromobenzamidoxime, O-methyl-ρ-bromobenzamidoxime and O-n-propyl-ρ-bromobenzamidoxime.

3. The method of claim 1, wherein the anhydrous gas is selected from the group consisting of nitrogen and argon.

4. The method of claim 1, wherein the anhydrous aprotic solvent is selected from the group consisting of dioxane and dimethylformamide.

5. The method of claim 1, wherein the palladium catalyst is tetrakis(triphenylphosphene)palladium m(0).

6. The method of claim 1, wherein the refluxing is for a period of about 16 hours.

7. The method of claim 1, further comprising:

(a) following the refluxing, removing the aprotic solvent to form a residue;

(b) diluting the residue into a nonpolar solvent to form a solvated residue;

(c) filtering the solvated residue to form a filtered residue;

(d) washing the filtered residue with a wash solvent to form a washed residue; and (e) drying the residue.

8. The method of claim 7, wherein the nonpolar solvent is selected from the group consisting of ethers, alkanes and methylene chloride.

9. The method of claim 7, wherein the wash solvent is selected from the group consisting of an ether, an alkane, methylene chloride, ethyl acetate, ethanol and combinations thereof.

* * * * *